United States Patent
Schaller

(10) Patent No.: US 9,192,377 B1
(45) Date of Patent: Nov. 24, 2015

(54) WORK HARDENING OF STAPLES WITHIN SURGICAL STAPLER

(75) Inventor: Michael P. Schaller, Palo Alto, CA (US)

(73) Assignee: Cardica, Inc., Redwood City, CA (US)

( * ) Notice: Subject to any disclaimer, the term of this patent is extended or adjusted under 35 U.S.C. 154(b) by 812 days.

(21) Appl. No.: 12/782,880

(22) Filed: May 19, 2010

Related U.S. Application Data

(60) Provisional application No. 61/183,376, filed on Jun. 2, 2009.

(51) Int. Cl.
*A61B 17/04* (2006.01)
*A61B 17/10* (2006.01)
*A61B 17/068* (2006.01)

(52) U.S. Cl.
CPC .................................... *A61B 17/068* (2013.01)

(58) Field of Classification Search
USPC ............................. 227/175.1–182.1; 606/219
See application file for complete search history.

(56) References Cited

U.S. PATENT DOCUMENTS

| | | | | |
|---|---|---|---|---|
| 2,880,540 A | * | 4/1959 | Williams | 428/10 |
| 3,117,757 A | * | 1/1964 | Sampson | 248/455 |
| 3,477,089 A | * | 11/1969 | Aaron | 16/16 |
| 3,650,453 A | * | 3/1972 | Smith, Jr. | 227/138 |
| 4,060,089 A | * | 11/1977 | Noiles | 606/220 |
| 4,127,227 A | * | 11/1978 | Green | 227/83 |
| 4,589,416 A | | 5/1986 | Green | |
| 5,818,186 A | * | 10/1998 | Camino | 318/434 |
| 5,833,695 A | * | 11/1998 | Yoon | 606/139 |
| 6,391,038 B2 | * | 5/2002 | Vargas et al. | 606/153 |
| 6,877,646 B2 | * | 4/2005 | Paynter | 227/120 |
| 7,918,376 B1 | * | 4/2011 | Knodel et al. | 227/175.1 |
| 7,954,683 B1 | * | 6/2011 | Knodel et al. | 227/175.1 |
| 7,963,432 B2 | * | 6/2011 | Knodel et al. | 227/175.1 |
| 7,988,026 B2 | * | 8/2011 | Knodel et al. | 227/175.1 |
| 2003/0035702 A1 | * | 2/2003 | Lin | 411/442 |
| 2004/0254608 A1 | * | 12/2004 | Huitema et al. | 606/219 |
| 2008/0078807 A1 | * | 4/2008 | Hess et al. | 227/181.1 |
| 2008/0210738 A1 | * | 9/2008 | Shelton et al. | 227/176.1 |
| 2010/0187285 A1 | * | 7/2010 | Harris et al. | 227/179.1 |
| 2010/0191255 A1 | * | 7/2010 | Crainich et al. | 606/142 |
| 2010/0191258 A1 | * | 7/2010 | Harris et al. | 606/144 |
| 2010/0191262 A1 | * | 7/2010 | Harris et al. | 606/151 |
| 2010/0191282 A1 | * | 7/2010 | Harris et al. | 606/219 |
| 2010/0230464 A1 | * | 9/2010 | Knodel et al. | 227/175.1 |

OTHER PUBLICATIONS

"Cardica Microcutter Implant Delivery Device 510(k), Cover Sheet, Table 10.1,"Substantial Equivalence Comparison,"and Section 12,"Substantial Equivalence Discussion, (Oct. 18, 2010).

\* cited by examiner

*Primary Examiner* — Robert Long
(74) *Attorney, Agent, or Firm* — Womble Carlyle Sandridge & Rice LLP

(57) ABSTRACT

An exemplary medical apparatus may include a surgical tool; a feeder belt located at least partially within the surgical tool; a plurality of staples affixed to and frangibly separable from the feeder belt; and a forming station positioned within the surgical tool that receives the feeder belt; where motion of the feeder belt through the forming station bends at least one staple relative to the feeder belt substantially at the junction between that staple and the feeder belt in order to work harden that junction within the surgical tool.

7 Claims, 2 Drawing Sheets

WORK HARDENING OF STAPLES WITHIN SURGICAL STAPLER

This application claims priority to U.S. Provisional Patent Application Ser. No. 61/183,376, filed on Jun. 2, 2009, which is herein incorporated by reference in its entirety.

FIELD OF THE INVENTION

The invention generally relates to surgical staplers and stapling.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. A linear cutter is a larger version of an endocutter, and is used to transect portions of the gastrointestinal tract. A typical endocutter receives at its distal end a disposable single-use cartridge with several rows of staples, and includes an anvil opposed to the cartridge. During actuation of an endocutter, the cartridge fires all of the staples that it holds. In order to deploy more staples, the endocutter must be moved away from the surgical site and removed from the patient, after which the old cartridge is exchanged for a new cartridge. The endocutter is then reinserted into the patient. However, it can be difficult and/or time-consuming to located the surgical site after reinsertion. Further, the process of removing the endocutter from the patient after each use, replacing the cartridge, and then finding the surgical site again is tedious, inconvenient and time-consuming, particularly where a surgical procedure requires multiple uses of the endocutter.

In order to overcome these difficulties, Cardica, Inc. of Redwood City, Calif. has developed a true multi-fire endocutter that is capable of firing multiple times without the need to utilize single-use-cartridges. Such an endocutter is described in, for example, U.S. Patent Application Publication No. 2009/0065552, published on Mar. 12, 2009 (the "Endocutter Publication"), which is hereby incorporated by reference herein in its entirety. Referring also to FIG. 1, that endocutter utilizes a feeder belt 2 to which staples 4 are fixed and frangibly separable therefrom. Each staple 4 has a free end 6, and an opposite end 8 that is fixed to the feeder belt 2. Each staple 4 is sheared from the feeder belt 2 at the junction between the end 8 of the staple 4 and the feeder belt 2. The staples 4 are perpendicular to the feeder belt 2 during advancement of the feeder belt 2, deployment of the staples 4, and shearing of the staples 4 from the feeder belt 2.

BRIEF DESCRIPTION OF THE DRAWINGS

The use of the same reference symbols in different figures indicates similar or identical items.

DETAILED DESCRIPTION

Figure 1:
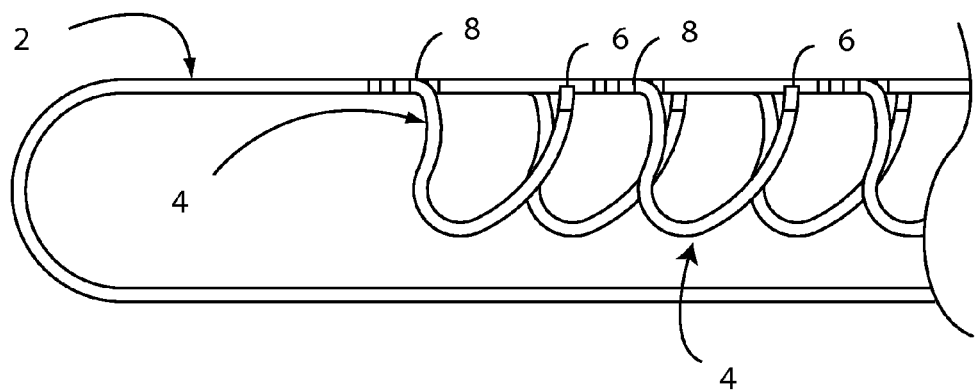
FIG. 1 is a side view of a feeder belt with staples affixed thereto.
Figure 2:
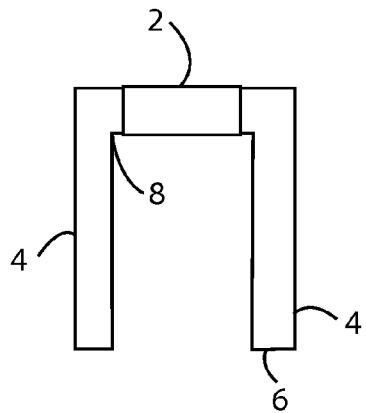
FIG. 2 is an end view of an exemplary feeder belt in a first configuration.

Referring also to FIG. 2, one example of a feeder belt 2 may include at least two surgical staples 4 attached to it, where each staple 4 initially extends downward from the feeder belt 2 at substantially a right angle. The initial orientation of the staples 4 relative to the feeder belt 2 may be different, if desired. Multiple staples 4 may be positioned on each side of the feeder belt 2, where each set of staples 4 is generally aligned in a row, as described in the Endocutter Publication.

One determinant of the location where each staple 4 will break away from the feeder belt 2 during deployment is the tensile strength of the material from which the feeder belt 2 and staples 4 are fabricated. Tensile strength at a particular location may depend on, among other factors, the material from which the feeder belt 2 and staples 4 are fabricated, heat treatment, and work hardening. In the case of 316L stainless steel, for example, the annealed tensile strength is approximately 85 ksi; the tensile strength for 90% cold-worked (i.e., work hardened) 316L stainless steel is as much as 224 ksi. Thus, work hardening a particular area may increase its tensile strength.

Figure 3:
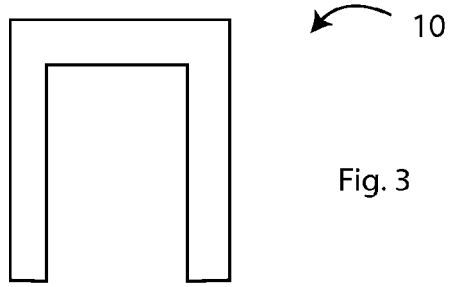
FIG. 3 is an end view of a passage in a surgical tool in which the feeder belt of FIG. 2 is received.

As one example, it may be desirable to anneal the feeder belt 2 and staples 4, then work harden the end 8 of the staple 4 attached to the feeder belt 2 and/or the portion of the feeder belt 2 to which that end 8 of the staple 4 is fixed. In this way, the softer, annealed portion of the staple 4 bends first during deployment in response to a first force, and the staple 4 is sheared from the feeder belt 2 in response to a second force greater than the first force. The junction between the feeder belt 2 and one or more staples 4 can be work hardened in a surgical tool in any suitable manner. As one example, referring to FIG. 3, the feeder belt 2 and staples 4 may be fed through a channel 10 defined in a surgical tool, where the shape of the channel 10 corresponds to the initial shape of the combined feeder belt 2 and staples 4. The channel 10 may change shape along its longitudinal direction (the direction perpendicular to the printed page). For example, referring to FIG. 4, the channel 10 may change shape to one in which the lateral portions of the channel 10 are angled outward. The channel 10 shaped as in FIG. 4—or any channel 10 shaped differently from the initial configuration of the channel 10—may be referred to as a forming station. As the feeder belt 2 is pulled longitudinally through the channel 10, it passes through the channel 10 as configured in FIG. 3. The channel 10 changes shape gradually until it reaches the shape of FIG. 4. Thus, as the feeder belt 2 is pulled longitudinally through the channel 10 into the forming station of FIG. 4, the staples 4 fixed to the feeder belt 2 are gradually bent outward relative to the feeder belt 2, where that bending is localized at the junction between each staple 4 and the feeder belt 2. That is, contact between the staples 4 and the bent-outward lateral portions of channel 10 causes those staples 4 to bend outward as well, as seen in FIG. 5. The channel 10 then gradually changes shape back to the configuration of FIG. 2, and the angle of the staples 4 relative to the feeder belt 2 returns to substantially the same angle as in the initial configuration of FIG. 2 as well. In this way, the junction between each staple 4 and the feeder belt 2 may be work hardened in the surgical tool. This work hardening may be considered the final step of manufacturing the staples 4.

Figure 4:
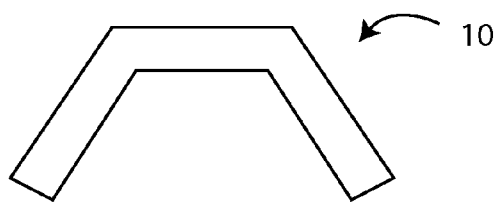
FIG. 4 is an end view of a forming station within a surgical tool in which the feeder belt of FIG. 2 is received and through which the feeder belt 2 is movable.
Figure 5:
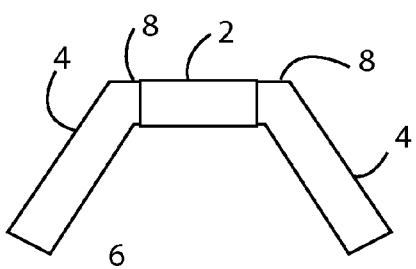
FIG. 5 is an end view of the exemplary feeder belt of FIG. 2 in a second configuration.

Alternately, the shape of the forming station of FIG. 4 may be different in order to increase or decrease bending of the staples 4 relative to the feeder belt 2, and thus increase or decrease the amount of work hardening at the junction between each staple 4 and the feeder belt 2. Alternately, the shape of the forming station of FIG. 4 may be different in order to concentrate bending in, and work harden, a different location in the feeder belt 2 and/or staples 4. Alternately, more than one forming station may be used, in order to work harden different locations in the feeder belt 2 and/or staples 4 each time, and/or to repeat one or more previous bends in order to further cold work a particular region.

Deployment and closure of the staples 4 otherwise may be performed substantially as set forth in the Endocutter Publication. While the present invention has been described with respect to the particular example of a feeder belt 2 and surgical staples 4 fixed to and frangibly separable from that feeder belt 2, it will be appreciated that the use of one or more forming stations, or any other structure or mechanism for cold working a part within a tool, may be used to alter the tensile strength of that part at a selected local area.

While the invention has been described in detail, it will be apparent to one skilled in the art that various changes and modifications can be made and equivalents employed, without departing from the present invention. It is to be understood that the invention is not limited to the details of construction, the arrangements of components, and/or the steps of performing anastomosis set forth in the above description or illustrated in the drawings. Therefore, the invention is not to be restricted or limited except in accordance with the following claims and their legal equivalents.

What is claimed is:

1. Apparatus; comprising:
a surgical tool;
a feeder belt located at least partially within said surgical tool;
a plurality of staples affixed to and frangibly separable from said feeder belt; and a forming station positioned within said surgical tool, wherein said forming station receives said feeder belt;
wherein motion of said feeder belt through said forming station bends at least one said staple in a first direction relative to said feeder belt substantially at the junction between each at least one staple and said feeder belt in order to work harden said junction within said surgical tool.

2. The apparatus of claim 1, wherein said motion of said feeder belt successively bends a plurality of said staples relative to said feeder belt.

3. The apparatus of claim 1, wherein motion of said feeder belt through said forming station additionally bends at least one staple in a second direction different from said first direction.

4. An apparatus, comprising:
a surgical tool;
a feeder belt located at least partially within said surgical tool;
a plurality of staples integral with and frangibly separable from said feeder belt; and
a channel within said surgical tool that receives said feeder belt;
wherein motion of said feeder belt through said channel bends at least one said staple at least at one location, thereby work hardening said staple at each location at which said staple bends.

5. The apparatus of claim 4, wherein the cross-section of said channel perpendicular to the longitudinal axis of said channel varies longitudinally along said channel.

6. The apparatus of claim 4, wherein at least part of said channel defines a closed perimeter about the longitudinal axis of said channel, and wherein said closed perimeter surrounds a portion of said feeder belt that is received into said channel.

7. The apparatus of claim 4, wherein said motion of said feeder belt through said channel is in the longitudinal direction.

\* \* \* \* \*